US010092265B2

(12) United States Patent
Lavallee et al.

(10) Patent No.: US 10,092,265 B2
(45) Date of Patent: *Oct. 9, 2018

(54) METHOD FOR RECONSTRUCTING A 3D IMAGE FROM 2D X-RAY IMAGES

(71) Applicant: SURGIVISIO, La Tronche (FR)

(72) Inventors: Stephane Lavallee, St Martin d'Uriage (FR); Markus Fleute, Volgelsheim (FR); Laurence Van Beek, St Martin d'Uriage (FR)

(73) Assignee: SURGIVISIO, La Tronche (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/438,523

(22) Filed: Feb. 21, 2017

(65) Prior Publication Data

US 2017/0164920 A1 Jun. 15, 2017

Related U.S. Application Data

(63) Continuation of application No. 15/031,108, filed as application No. PCT/EP2014/073535 on Nov. 3, 2014, now Pat. No. 9,610,056.

(30) Foreign Application Priority Data

Nov. 4, 2013 (EP) ...................................... 13306508

(51) Int. Cl.
*G06K 9/00* (2006.01)
*A61B 6/00* (2006.01)
(Continued)

(52) U.S. Cl.
CPC ............ *A61B 6/5235* (2013.01); *A61B 6/032* (2013.01); *A61B 6/0407* (2013.01);
(Continued)

(58) Field of Classification Search
CPC ..... A61B 6/5235; A61B 6/584; A61B 6/5205; A61B 6/441; A61B 6/032; A61B 90/39; G06T 11/006; G06T 2211/424
See application file for complete search history.

(56) References Cited

U.S. PATENT DOCUMENTS 5,335,260 A * 8/1994 Arnold .................... A61B 6/505
378/18
6,157,747 A * 12/2000 Szeliski ................ G06K 9/209
345/419
(Continued)

FOREIGN PATENT DOCUMENTS

| EP | 2546804 A1 | 1/2013 |
| WO | WO-2009081297 | 7/2009 |

OTHER PUBLICATIONS

International Search Report and Written Opinion in PCT/EP2014/073535 dated Feb. 9, 2015. 7 pages.
(Continued)

*Primary Examiner* — John Strege
(74) *Attorney, Agent, or Firm* — Womble Bond Dickinson (US) LLP

(57) ABSTRACT

The present invention relates to a method for reconstructing a 3D image from 2D X-ray images acquired with an X-ray imaging system, said method comprising the steps of:
 a) receiving a set of 2D X-ray images of a region of a patient with said X-ray imaging system,
 b) computing an initial 3D image within the coordinate system of the X-ray imaging system by using at least part of said 2D X-ray images with their respective projective geometry data;
 c) projecting said initial 3D image on at least part of said 2D X-ray images and adjusting the respective projective geometry data of said images, said adjustment
(Continued)

comprising registration of said images with the projection of the initial 3D image using an image-to-image registration technique;

d) computing an updated 3D image using the complete set of 2D X-ray images with their respective adjusted projective geometry data.

6 Claims, 6 Drawing Sheets

(51) Int. Cl.
*A61B 6/03* (2006.01)
*G06T 11/00* (2006.01)
*A61B 90/00* (2016.01)
*A61B 6/04* (2006.01)
*G06T 7/00* (2017.01)

(52) U.S. Cl.
CPC .......... *A61B 6/4405* (2013.01); *A61B 6/4441* (2013.01); *A61B 6/5205* (2013.01); *A61B 6/584* (2013.01); *A61B 90/39* (2016.02); *G06T 7/0012* (2013.01); *G06T 11/006* (2013.01); *A61B 2090/3966* (2016.02); *G06T 2207/10116* (2013.01); *G06T 2207/20048* (2013.01); *G06T 2211/424* (2013.01)

(56) References Cited

U.S. PATENT DOCUMENTS

| | | | | |
|---|---|---|---|---|
| 8,233,586 | B1* | 7/2012 | Boas | G06T 11/005 378/207 |
| 8,666,137 | B2* | 3/2014 | Nielsen | G06T 11/005 382/131 |
| 9,135,729 | B2* | 9/2015 | Wein | G06T 11/008 |
| 2003/0181809 | A1* | 9/2003 | Hall | A61B 6/12 600/425 |
| 2005/0068466 | A1* | 3/2005 | Waters | H04N 9/28 348/745 |
| 2009/0051679 | A1* | 2/2009 | Robinson | G06T 7/246 345/418 |
| 2010/0014726 | A1* | 1/2010 | Schaefer | A61B 6/032 382/128 |
| 2011/0038042 | A1* | 2/2011 | Redmann | G03B 35/18 359/462 |
| 2012/0045108 | A1* | 2/2012 | Shechter | G06T 11/005 382/131 |
| 2013/0010920 | A1* | 1/2013 | Wein | G06T 11/008 378/19 |
| 2013/0085387 | A1* | 4/2013 | Chen | A61B 8/085 600/439 |
| 2013/0223719 | A1* | 8/2013 | Ohishi | A61B 6/5235 382/132 |
| 2013/0243293 | A1* | 9/2013 | Dennerlein | G06T 11/008 382/131 |
| 2014/0031664 | A1* | 1/2014 | Kang | A61B 6/4405 600/407 |
| 2014/0369463 | A1* | 12/2014 | Thibault | G01N 23/046 378/19 |
| 2015/0078642 | A1* | 3/2015 | Fang | A61B 5/14553 382/131 |

OTHER PUBLICATIONS

Wein et al. "Self-Calibration of Geometric and Radiometric Parameters for Cone-Beam Computed Tomography." 11th International Meeting on Fully Three-Dimensional Image Reconstruction in Radiology and Nuclear Medicine (Jul. 15, 2011). 4 pages.

European Search Report and Written Opinion, dated Apr. 12, 2017, European Application No. EP16207448.

* cited by examiner

METHOD FOR RECONSTRUCTING A 3D IMAGE FROM 2D X-RAY IMAGES

FIELD OF THE INVENTION

This invention generally relates to medical X-ray imaging systems, specifically to methods and devices for improving the quality of 3D images reconstructed from a set of 2D projection images.

BACKGROUND OF THE INVENTION

X-Ray imaging systems are frequently used during medical surgical procedures and interventions to provide physicians with image based information about the anatomical situation and/or the position and orientation of surgical instruments.

These devices typically provide two-dimensional projection images with different structures superimposed along the path of the X-rays.

A typical example of such a device for use in an intra-operative setting is the so-called C-arm used in a mobile or stationary manner and essentially consisting of a base frame on which a C-shaped arm is attached with several intermediate joints allowing moving the C-shaped arm in space along several degrees of freedom.

One end of the C-shaped arm carries an X-ray source and the other end an image detector.

Due to the limited information provided by these 2D images, 3D imaging techniques have become indispensable over the past decades.

While computer tomography is a well-established class of stationary X-ray imaging systems used for 3D reconstruction in a radiology department, these devices are in general not usable inside the operating room.

Recent years have seen an increasing interest in tomographic reconstruction techniques also known as cone-beam reconstruction techniques using two-dimensional detectors. Background information on these reconstruction techniques can be found, for example, in [1, 2].

Special efforts have been made to enable the abovementioned C-arms to provide three-dimensional information by automatically acquiring a set of 2D images and subsequent 3D image reconstruction based on said cone-beam reconstruction techniques [3-13].

Recently, so-called Cone-Beam Computer Tomography systems have been introduced to produce 3D images of patient parts, for example for dentistry applications, by simply creating a complete rotation of a source and an image plane contained inside a closed torus. This can be seen as a particular design of a C-arm.

In order to obtain high quality 3D images in terms of spatial resolution, geometric fidelity etc., it is essential to precisely know the projection geometry i.e. the position and orientation of the source and the detector in a common referential system for each 2D image used for the reconstruction.

However, while very well adapted to intra-operative 2D imaging tasks thanks to their maneuverability, C-arms, originally not designed for 3D imaging, are mechanically not sufficiently rigid to reproduce the desired projection geometry along a chosen path with sufficient accuracy due to their open gantry design.

The nominal trajectory of a C-arm during the automatic 2D image acquisition can be easily measured, for instance with encoders integrated in the joints.

However, the real trajectory differs from the nominal one for different reasons similar to the true kinematics and its nominal model in the field of robotics. The open gantry design makes the device prone to mechanical distortions such as bending depending on the current position/orientation. In particular, mobile C-arms are prone to collisions with doors or other objects while moved around, resulting in non-elastic deformations of the C-arm. Depending on the type of bearing and drive of the C-arm, wobbling of the C-arm cannot be avoided due to its own mass and the masses of the x-ray source and x-ray detector altering the nominal trajectory thus leading, as a geometry error, to limitation of the spatial resolution of the reconstructed 3D image.

To overcome these problems, different methods are known from the literature for calibrating the imaging geometry of the C-arm i.e. to measure the projection geometry for the trajectory used for acquiring the images.

The term projection geometry, as used here, encompasses the detector position and orientation, as well as the X-ray source position relative to a common referential system.

A common technique consists in using a well-defined calibration phantom that allows precise determination of the entire projection geometry for each image taken throughout a scan, such that the predicted marker projections based on that geometry and a model of the phantom optimally match the locations of the markers identified in the image. Such a calibration phantom, which is rather cumbersome due to its required volumetric expansion to allow determination of the entire projection geometry, can be used either online (i.e. during each diagnostic use) or offline (i.e. not during diagnostic use).

In practice, the general approach to offline calibrating an imaging system consists in performing an image acquisition of a specific calibration phantom containing radiopaque markers prior to the diagnostic image acquisition. The phantom remains stationary during the scan. The projection images are then evaluated in a pre-processing step in order to extract marker shadow locations and correspondences from the images. This is followed by the calibration step itself, which establishes the optimal estimate of the projection geometry for each projection, usually based on an estimation error metric which is often the root-mean-square error between the detected and the predicted marker shadow locations, based on the current estimate of the projection geometry.

U.S. Pat. Nos. 6,715,918 and 5,442,674 disclose such an offline calibration phantom consisting essentially of a radiotransparent cylindrical tube with radiopaque markers of different size attached to its circumference at precisely known positions. During the calibration process, a series of images is taken throughout the trajectory chosen for image acquisition with the phantom being placed such that the markers are visible in all images without repositioning the phantom. Using well-known image processing methods, marker centers are calculated in the projection images and labelled, i.e. assigned to the corresponding marker in the phantom having caused the shadow in the image. With sufficient marker centers calculated and assigned, the projection geometry for all images can then be computed in a common referential system.

Calibration with such an offline phantom is typically carried out once before the first clinical use of the system and subsequently at longer or shorter intervals, e.g. every 6 months. By its nature this method deals well with reproducible deviations.

On the other hand, irreproducible deviations of the projection geometry like thermal shifts, fatigue over time, mechanical deformations due to collisions of the device during use or transport cannot be compensated for.

Since deviations can only be detected during the offline calibration, there is a risk that at one point in time, between two recurring offline calibrations, the 3D images will lack the accuracy necessary for clinical use. Another drawback of offline calibration methods is to restrict the use of the C-arm for 3D reconstruction to only one trajectory, i.e. the one that has been calibrated.

In order to allow compensation for irreproducible errors as well, different online calibration methods are known from the literature.

These methods aim at performing the calibration during the diagnostic image scan of the device, using a phantom made of radiopaque markers that are placed in the volume to be acquired and reconstructed as a 3D image.

One of the general problems with such an online calibration method based on radiopaque markers aiming at a full calibration, i.e. determining the complete projection geometry for each acquired image, is the fact that for diagnostic imaging, the C-arm is positioned such that the anatomical region of interest (ROI) is visible on each image.

Since the phantom can obviously not be placed exactly in the same position, it is usually difficult—if not impossible—to ensure the visibility of the phantom in all images, thus often not allowing a full calibration.

Another problem is that radiopaque or very radio-dense objects such as metal parts of the operating table, surgical instruments, implants etc. may occlude one or more of the phantom markers in one or more of the images.

U.S. Pat. No. 6,038,282 aims at solving this problem by positioning an online arc-shaped phantom around the patient, essentially working in the same manner as the offline calibration method described above. However, while providing potentially good calibration accuracy, this phantom significantly obstructs the surgical access to the patient and is very cumbersome and expensive to manufacture and maintain with high mechanical accuracy.

To overcome these problems other methods for online calibration have been proposed.

U.S. Pat. No. 6,079,876 discloses a method for online calibration based on optical cameras attached to both ends of the C-shaped arm allowing determination of the position and orientation of both the detector and the source with respect to an optical marker ring positioned around the operating table. The marker ring required in this method complicates the access to the patient and must be repositioned each time the C-arm position or orientation is adjusted.

U.S. Pat. No. 6,120,180 discloses a method for online calibration using an ultrasound or electromagnetic tracking system in order to capture the position and orientation of both the source and the detector. This system is prone to occlusion and magnetic field distortion problems as well as ergonomic restriction preventing these systems from being used in a clinical environment.

DE 10139343 discloses a method for online calibration based on strain gauges to measure the deflection of the C-arm. This method is complex to manage and maintain with a high degree of accuracy over time, and it cannot recover the full projection geometry and captures only some deformations.

U.S. Pat. No. 7,494,278 discloses a calibration method that dispenses with any additional measuring equipment by seeking to use natural features in the projection images themselves to detect and correct for trajectory deviations visible in sinograms. While this method could in theory be effective, it is not revealed how image features to be tracked in sinograms are identified. No method for detecting such natural features with a high degree of precision and reproducibility is described, which makes it non-usable in reality.

Accordingly, the present invention is intended to improve the quality of reconstructed 3D image by overcoming at least one of the above disadvantages.

SUMMARY OF THE INVENTION

The present invention provides a method for improving the reconstruction quality of a 3D image, especially in relation with mobile X-ray imaging systems used for intraoperative 3D imaging in orthopedics, traumatology and other surgical or diagnostic fields.

This method comprises the steps of:

a) receiving a set of 2D X-ray images of a region of a patient with said X-ray imaging system, b) computing an initial 3D image within the coordinate system of the X-ray imaging system by using at least part of said 2D X-ray images with respective projective geometry data;

c) projecting said initial 3D image on at least part of said 2D X-ray images and adjusting the respective projective geometry data of said images, said adjustment comprising registration of said images with the projection of the initial 3D image using an image-to-image registration technique;

d) computing an updated 3D image using the complete set of 2D X-ray images with their respective adjusted projective geometry data.

By computing an initial 3D image and using a projection of said initial 3D image for registration of a 2D X-ray image and the projection of the initial 3D image, it is possible to adjust the projective geometry data of the 2D X-ray images.

Hence, the adjusted projective geometry data take into account the non-reproducible positioning deviations of the source and detector of the X-ray imaging system not covered by the nominal projective geometry data.

The adjusted projective geometry data can then be used to compute an updated image with greater accuracy.

The above-described steps may be iterated until the required accuracy is obtained.

The above-described method offers a general solution to online calibration of C-arms that can be used practically and realistically, thus offering significant improvement of accuracy and sharpness of 3D image reconstruction over known methods. In such a way, the present invention overcomes the problems known in today's devices, namely the lack of sufficient accuracy and fidelity of 3D reconstruction and respectively the lack of clinical applicability of phantoms currently available for online calibration improvement. In addition, the present invention is intended to solve the issue wherein not only the imaging device is slightly deformed with respect to its nominal calibration, but also some of patient motions that may occur during the image acquisition, due for example to breathing, have to be compensated for.

Some markers are used in order to reinforce the robustness and accuracy of the method, which can be used even if the nominal parameters are known with poor accuracy. The invention allows increasing the quality of the reconstructed 3D image or volume by refining the projective geometry data for each acquired 2D image by adjusting, in conformity with the invention, nominal projective geometry data known from design, encoders or offline calibration methods, based on the information provided by a variable quantity of radiopaque markers detectable in a variable subset of the complete set of acquired 2D images. In that particular embodiment, at least one marker is needed. In the present text, "detectable" means that the respective marker can be automatically detected by software in a given image, because it is in the field of view for said image and it is not hidden partially or totally by a body structure such as a bone. Hence, a marker can be detectable in some images and not detectable in other images.

In a first aspect, the 3D reconstruction uses a set of 2D X-ray images of a region of a patient wherein a calibration phantom containing radiopaque markers is placed close to the anatomical region of the patient to be examined during the acquisition of said set of 2D X-ray images.

The phantom may be attached to the patient either invasively, e.g. via a clamp, screws or pins, or non-invasively, with an adhesive patch for example. The radiopaque markers can vary in number (at least one radiopaque marker is necessary) and they can be of different shapes such as ball-shaped or cylinder-shaped.

In one embodiment, radiopaque markers are ball-shaped.

In another embodiment, radiopaque markers are needle-shaped.

In one embodiment, the calibration phantom comprises radiopaque markers covered by reflective material detected by an optical localizer.

In one embodiment, the calibration phantom comprises surgical implants.

In another embodiment, radiopaque markers are constituted by electromagnetic coils, said electromagnetic coils being used for constituting transmitters or receivers of electromagnetic localization devices embedded in surgical navigation systems.

In another embodiment, radiopaque markers are a combination of ball-shaped, needle-shaped markers and/or electro-magnetic coils.

By using a support structure incorporated into the calibration phantom, the markers have a fixed spatial relationship to each other, which is known by design or metrological measurements. Such metrological measurements are preferably performed before the first use, and at repeated intervals. In another preferred embodiment, such metrological measurements of the relative positions of the markers are performed just at the beginning of the image acquisition using a 3D localization device (optical, electro-magnetic, etc.), such 3D localization device being a component of any standard surgical navigation system.

Typical X-ray imaging systems targeted by the invention comprise an X-ray source and an image detector supported by a mobile arm with a plurality of degrees of freedom to position and orient the X-ray source and the detector in space, and a data processing unit.

During a scan, a set of 2D images is acquired, each image corresponding to a slightly different position of the source-detector couple.

In addition to the anatomical structures under examination, X-ray shadows generated by the phantom markers will appear on a subset of the acquired 2D images, whereas the number of the 2D images containing marker shadows that are detected by software depends on the phantom geometry and its positioning with respect to the trajectory of the source-detector couple during a scan.

On the other hand, at least one 2D image does not contain any automatically detectable marker.

After the scan, in a first step, all images containing markers that can be detected automatically by software are selected, and the positions of all detected markers within those images are calculated precisely by the data processing unit. Such images containing automatically detected markers are labeled as reference images, whereas the remaining images are considered as non-reference images.

An optimal rigid transformation between a coordinate system of the X-ray imaging system and the coordinate system of the calibration phantom is then computed by optimizing the registration between the known 3D position of at least one marker of the calibration phantom and the corresponding 2D position of said marker detected in at least two different reference images using nominal projective geometry data of said X-ray imaging system, such that the distance between the projections of the 3D position of the marker in each reference image and the corresponding 2D position in said reference images is minimized.

Said optimal rigid transformation is applied to the 3D position of said at least one marker of the calibration phantom to determine its respective transformed 3D position in the coordinate system of the X-ray imaging system.

For each of the reference images, adjusted projective geometry data are computed from the 2D position of the at least one marker detected in said reference image and said transformed 3D phantom marker position, such that the projection of said transformed 3D position using the adjusted projective geometry data fits optimally with the 2D position of corresponding marker.

Then a reconstructability criterion that characterizes the ability to reconstruct a 3D image with sufficient quality from the reference images only is calculated.

In step b), the computation of the initial 3D image within the coordinate system of the X-ray imaging system is implemented by using:
    if said reconstructability criterion is met, the reference images with their respective adjusted projective geometry data; or
    if said reconstructability criterion is not met, the reference images with their respective adjusted projective geometry data and the non-reference images with their respective nominal projective geometry data.

In step c), the initial 3D image is projected on the non-reference images, the respective nominal projective geometry data of the non-reference images being adjusted by registration of said non-reference images with said projected 3D image using an image-to-image registration technique.

In step d), the computation of the updated 3D image uses the complete acquired set of 2D X-ray images with their respective adjusted projective geometry data.

According to one embodiment, one or several of the steps described above are iterated until a registration quality measure is below a predetermined threshold or a predetermined number of iterations has been reached.

When the selection step is iterated, the new iteration uses the projection of the at least one marker of the phantom whose position is known in the coordinate system of the X-ray imaging system after the previous registration step has been performed in order to improve the number of markers that are automatically detected.

According to one embodiment, the optimal rigid transformation is computed as a best fit between the 3D phantom marker position and the 2D position of the marker detected in said reference images, back-projected according to said nominal projective geometry data.

According to one particular embodiment, only one marker of said calibration phantom is detected on at least two 2D images, and the optimal rigid transformation is a translation.

According to one embodiment, the modifications applied to the nominal projective geometry data for computation of said adjusted projective geometry data for each reference 2D image consist of modifications of the position of the X-ray source in a plane parallel to the image detector.

According to one embodiment, the adjustments applied to the nominal projective geometry data of said non-reference images in step (c) are limited to translation and rotation in a plane parallel to the image detector.

According to one embodiment, at least one radiopaque marker is automatically detected in at least two of said acquired 2D X-ray images, which form an angle of at least 15° to each other.

According to one embodiment, the calibration phantom comprises only one or two radiopaque marker(s).

According to one embodiment, the calibration phantom comprises localizing elements that enable the navigation of a surgical instrument in the reconstructed 3D image.

BRIEF DESCRIPTION OF THE DRAWINGS

Further features, effects and advantages of the invention will be apparent from the detailed description that follows, with reference to the appended drawings wherein.

DETAILED DESCRIPTION OF THE INVENTION AND PREFERRED EMBODIMENTS

Figure 1A:
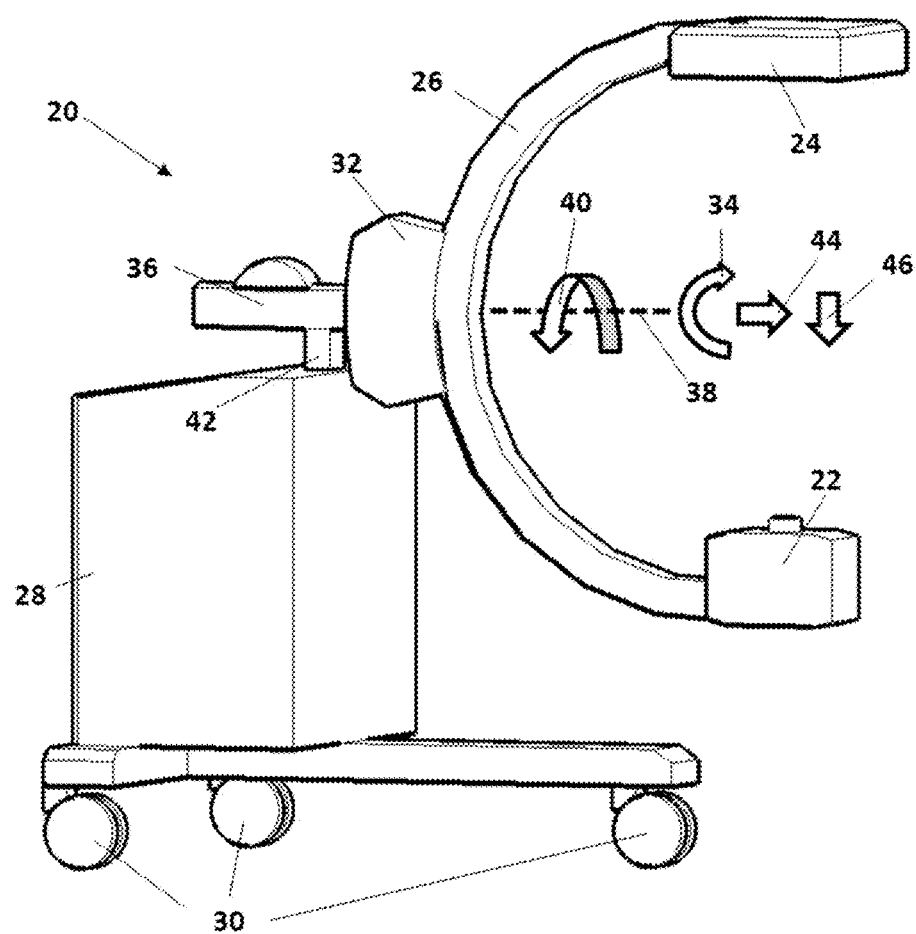
FIG. 1a schematically illustrates an exemplary embodiment of an X-ray imaging with a multitude of degrees of freedom.

FIG. 1a depicts one embodiment of a mobile X-ray imaging system 20 comprising an X-ray source 22, an X-ray detector 24, a C-shaped arm 26, and a chassis 28 with attached rollers 30.

The X-ray source 22 is attached at one end of C-shaped arm 26 and the X-ray detector 24 is attached at the other end of C-shaped arm 26.

The X-ray source 22 and the detector 24 are mounted facing each other on opposing ends of the C-shaped arm 26 in a manner known in the art.

The 2D images captured by detector 24 can be transmitted to a graphic display not shown in the figure for direct visualization.

The 2D images may also be stored in a memory of a data processing unit of the X-ray imaging system.

Said data processing unit (not illustrated) typically comprises a processor that is adapted in particular to compute a 3D image from a set of acquired 2D images, to compute transformations between different coordinate systems, etc.

The data processing unit further comprises a memory for storing the acquired images, the parameters of the imaging system (in particular, the nominal projective geometry data), and the results of the computations.

As FIG. 1a further illustrates, C-shaped arm 26 is mounted to a holder 32, which allows the C-shaped arm 26 to move along its circumference while sliding in the holder thus accomplishing an orbital rotation as indicated by arrow 34.

The holder 32 is linked to a horizontal guide 36 allowing horizontal translational movement of C-shaped arm 26 as indicated by arrow 44 and angular rotation around angular rotation axis 38 as indicated by arrow 40.

The horizontal guide 36 is mounted on a vertical column 42, for vertical translational movement of C-shaped arm 26 as indicated by arrow 46.

Table 1 summarizes the degrees of freedom the imaging system provides with its different joints.

TABLE 1

| Ref. | Degree of freedom | Description |
| --- | --- | --- |
| 34 | orbital movement | rotation of C-shaped arm 26 along its circumference in holder 32 |
| 40 | angular movement | rotation of holder 32 and therewith of C-shaped arm 26 around angular rotation axis 38 |
| 44 | horizontal movement | translation of holder 32 and therewith of C-shaped arm 26 in horizontal guide 36 |
| 46 | vertical movement | translation of horizontal guide 36 and therewith of holder 32 and C-shaped arm 26 in a vertical direction along column 42 |

It must be noted that it is not important for the invention that the imaging system implements exactly the kinematics that has been described above with its associated degrees of freedom, but rather many possible architectures with multiple degrees of freedom can be selected.

It is for example possible that the imaging system includes an additional rotational degree of freedom around the vertical column 42 without this having any impact on the invention. It can also include a translation of the mobile device on the floor, orthogonally to the C-shaped plane.

It is also possible to use architectures in which the function of the C-shaped arm is performed by a multi-axis robot like the Syngo device from Siemens, or simple Cone Beam Computer Tomography (CBCT) architectures commonly used in dentistry like the i-CAT system from Imaging Science International for example.

Some or all of the joints are equipped with position encoders as known in the art and not shown in the figure. It is also possible to use some global tracking systems consisting of gyroscopes and accelerometers in combination with or replacement of encoders.

The measurements of these encoders can be transmitted to the data processing unit of the X-ray imaging system 20.

In certain embodiments of the invention, some or all of the joints can be locked by brakes, either individually or in combination.

In certain embodiments, adjustment of the different joints is carried out using electric motors not shown in the figures. The motors may be controlled by the data processing unit.

According to a preferred embodiment, a calibration phantom is used so as to provide markers that are detectable on at least a part of the set of 2D X-ray images.

Figure 1B:
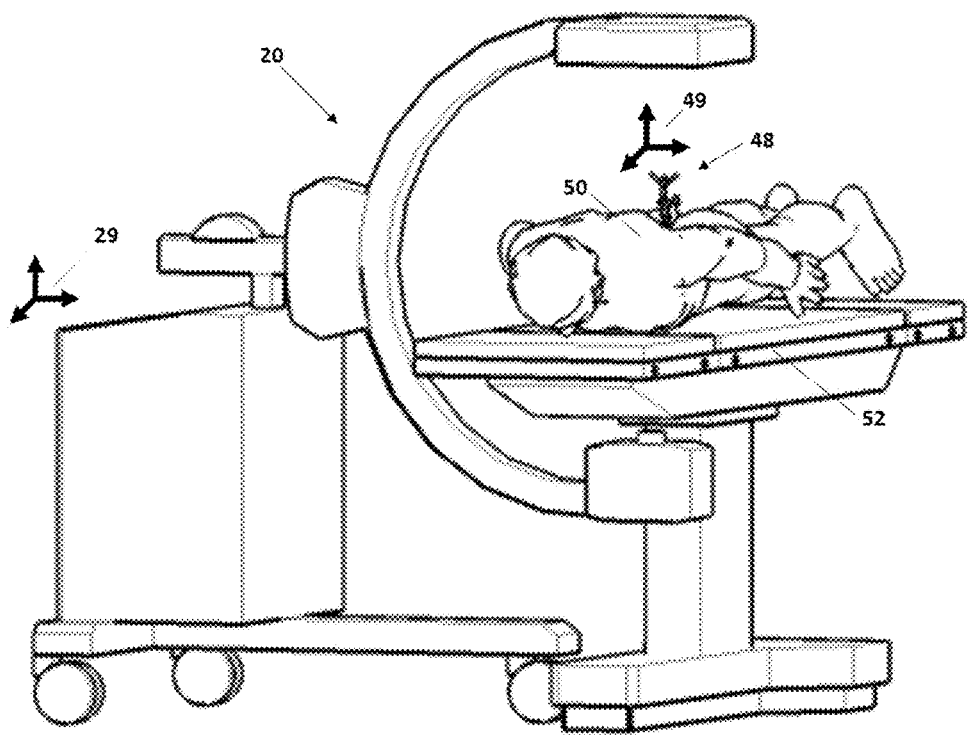
FIG. 1b schematically illustrates an exemplary embodiment of an X-ray imaging system with a phantom attached to a patient under examination.

FIG. 1b depicts a calibration phantom 48 attached to a patient 50 lying on a patient table 52.

Mobile X-ray imaging system 20 is positioned with respect to patient table 52, patient 50 and phantom 48, such that the movements of imaging system 20 during a scan are not impeded, i.e. no collisions occur.

The calibration phantom has the following constituents:

One or more X-ray opaque markers made e.g. out of steel, titanium, tantalum or aluminum, with known shapes such as balls or cylinders or thin tubes, or a combination of them, constitute the functional components for the calibration process. Markers may have also complex shapes that correspond to known models of surgical instruments or implants.

In one preferred embodiment, all markers are rigidly attached to a substantially radio-transparent support structure such as polyether ether ketone (PEEK), or Plexiglas, or carbon fiber for instance, for establishing and maintaining a fixed known spatial relationship between the markers. The position of all markers is known precisely by design or metrological measurements in a coordinate system 49 linked to the calibration phantom. Such metrological measurements are preferably performed before the first use, and at repeated intervals. In another preferred embodiment, such metrological measurements of the relative positions of the markers are performed just at the beginning of the image acquisition using a 3D localization device (optical, electro-magnetic, etc.), such 3D localization device being a component of any standard surgical navigation system.

The calibration phantom is designed such that differences in marker shape and size, together with the known relative positioning of the markers to each other, allow identifying them from the shadows they generate in an X-ray projection image. Multiple methods have been described in the literature to automatically detect and identify markers on X-ray or video images.

In certain embodiments, the calibration phantom further comprises an attachment fixture for attaching the support structure supporting the markers to the patient during the scan. Said attachment fixture creates a stable spatial relationship between the X-ray calibration phantom and the anatomical structure to be examined throughout the duration of the scan. As explained below, the attachment fixture may comprise various embodiments and shapes that can be selected by the practitioner depending on the region of the patient that has to be imaged and also based on considerations about the invasiveness of the fixation solution.

In a certain embodiment the calibration phantom further comprises a localization component rigidly connected to the support structure allowing detection of the position of the phantom, and therewith of coordinate system 49 in space, with a localization system. This makes it possible to correlate the 3D reconstruction directly to a surgical navigation system as described in U.S. Pat. No. 7,672,709 for example.

The localization system may be based on different technologies used alone or in combination such as optical with passive reflective markers, optical with active emitting markers, electromagnetic, gyroscope, accelerometer, RFID, ultrasonic, etc. and the localization component differs accordingly.

In one preferred embodiment, the calibration phantom contains electromagnetic coils that are transmitters and/or sensors of a localization device which is part of a surgical navigation system. The surgical instruments equipped with electromagnetic sensors or transmitters can therefore be localized directly with respect to a coordinate system attached to the calibration phantom. Using the method of the invention, the reconstructed 3D image is known in the coordinate system attached to the phantom. Therefore, the surgical instrument position and orientation can be displayed and navigated directly on the reconstructed 3D image, using many possible 2D or 3D visualization formats. Additional spherical or linear markers can be added in order to reinforce the accuracy and ease of automated detection and labeling of markers. In said preferred embodiment, the calibration phantom contains localizing elements that enable the navigation of a surgical instrument in the reconstructed 3D image. The same principle applies to an optical localizer.

Figure 2:
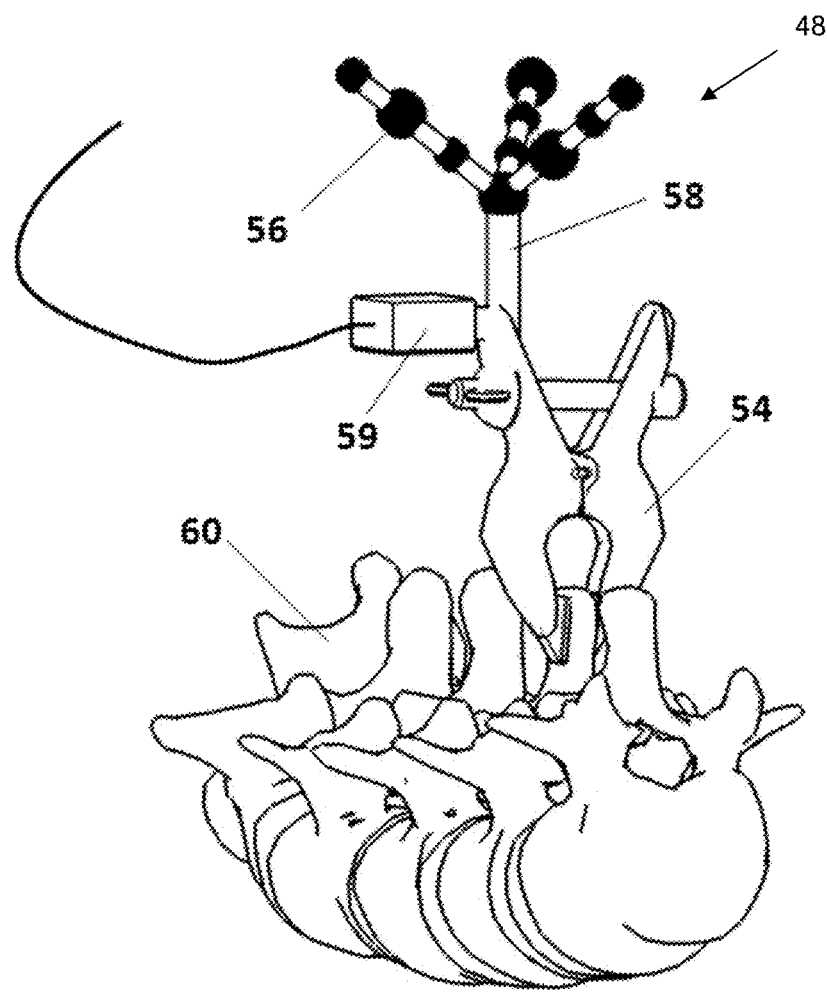
FIG. 2 schematically illustrates an exemplary embodiment of a phantom with radiopaque markers and a clamp fixation.

FIG. 2 schematically illustrates an exemplary embodiment of calibration phantom 48 wherein the attachment fixture consists of a clamp 54.

Spherical shaped radiopaque markers 56 are attached to support structure 58 which is itself connected to clamp 54.

The clamp 54 is attached to a vertebral body 60 to establish a rigid spatial relationship between the calibration phantom and said vertebral body.

Localization component 59 contains electro-magnetic coils and is connected to an electromagnetic localization system (not shown in the figure) thus allowing determination of the position of phantom 48.

Figure 3:
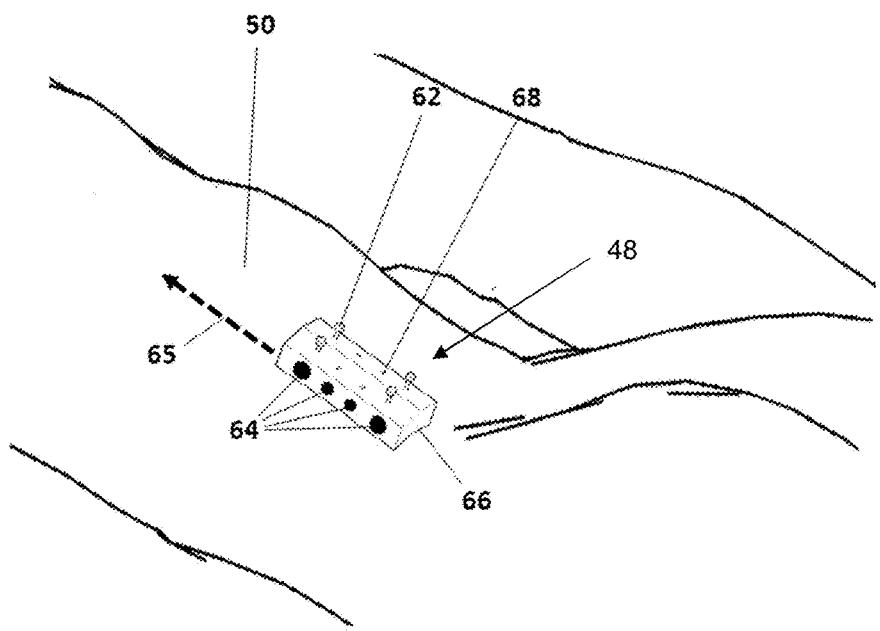
FIG. 3 schematically illustrates an exemplary embodiment of a phantom with radiopaque markers and pin fixation.

FIG. 3 schematically illustrates an exemplary embodiment of calibration phantom 48 wherein the attachment fixture consists of a plurality of pins 62.

Figure 4:
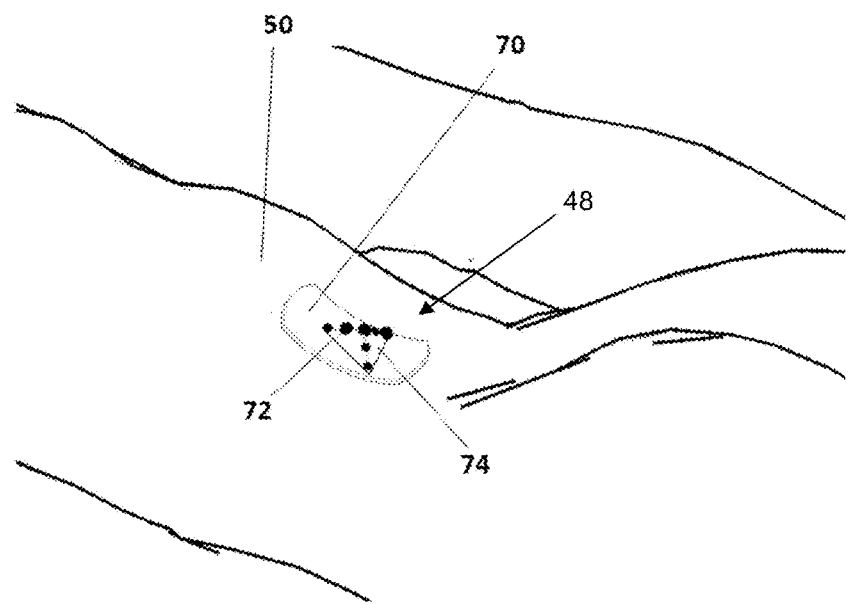
FIG. 4 schematically illustrates an exemplary embodiment of a phantom with radiopaque markers and adhesive patch fixation.

Radiopaque markers 64 are attached to support structure 66 which further contains feed holes 68 for attaching the phantom to patient 50 with pins 62. Multiple feed holes are used and the pins have sharp tips that are simply inserted into a bone of the patient by applying a pressure, like for a tack in a wall, the rigidity being created by the large number of pins. The support structure 66 might also contain electromagnetic sensors or transmitters which are not represented. FIG. 4 schematically illustrates an exemplary embodiment of calibration phantom 48 wherein the attachment fixture consists of an adhesive patch 70.

Radiopaque markers 72 are attached to support structure 74.

Adhesive patch 70, which is firmly fixed to support structure 74, can be adhesively attached to an anatomical structure, e.g. the skin of the patient 50.

Multiple spherical markers 72 are represented.

In one preferred embodiment, part or all of markers 56, 64 or 72 are covered by reflective materials to be tracked by an optical localizer of a surgical navigation system. In another preferred embodiment, the spherical markers 56, 64 or 72 are modified reflective spheres commonly used in optical surgical navigation, for example a metal sphere is inserted at the center of a standard navigation plastic sphere covered by retro-reflective tape (such as the ones produced by Northern Digital Inc., Ontario, Canada).

In another preferred embodiment, part or all of markers 56, 64 or 72 may be also standard reflective plastic non radiopaque balls but the post on which they are usually clipped on contains a metal ball that coincides perfectly with the center of the reflective ball when the ball is clipped on it.

In another embodiment, the markers 56, 64 or 72 are metal balls dedicated to calibration only and they make part of a rigid body, like 66 or 74, that contains standard navigation plastic spheres (that are usually non radiopaque).

In a preferred embodiment, the calibration phantom contains only three or four reflective spheres that define a unique rigid body position and orientation using an optical localizer of a surgical navigation system, and the inside of each reflective sphere contains a radiopaque small sphere, using one of the techniques described above. This represents a minimal structure for the calibration phantom if it is expected to obtain the calibration of the C-arm as described in this invention as well as the conventional tracking as it is used in optical surgical navigation systems at the same time.

However, in one preferred embodiment, only one marker is fixed to the adhesive patch, which makes it very simple to use and cheap to manufacture.

In another preferred embodiment, two markers are fixed to the adhesive patch and placed in a line parallel to the body axis such that the markers will not superimpose when multiple 2D images are acquired around the body axis.

Using a small number of markers fixed to an adhesive patch fixed to the patient skin has the advantage to be non-invasive and therefore usable in pure diagnostic examinations wherein no surgical intervention is performed or wherein no surgical navigation is intended to be used.

The accuracy of the method will then depend on the relative stability between the part of the skin where the adhesive patch is fixed and the anatomical structure of interest.

An adhesive patch fixed to the back of a patient will be very suitable to get accurate images of vertebrae for example, even if the patient breathes during the image acquisition.

This feature applies to any embodiment of the invention and represents a significant advantage.

Using radiopaque features that are close and relatively fixed to the region to be imaged, the accuracy of the 3D reconstruction will be improved in said region, even in the presence of patient breathing or motions.

Of course, this feature has some limitations and the final accuracy and patient motion compensation will depend on the number of reference images wherein the markers are detected and on the characteristics of the histogram for the images that will be registered using image-to-image registration techniques.

Figure 5:
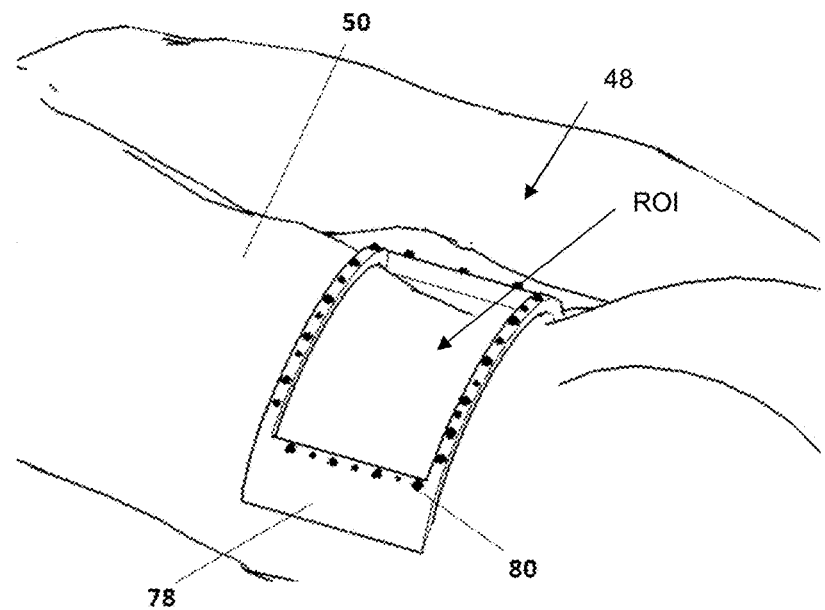
FIG. 5 schematically illustrates an exemplary embodiment of a phantom with radiopaque markers and a bow shaped support.

FIG. 5 schematically illustrates a preferred embodiment of calibration phantom 48 with a support structure 78 shaped like a frame being bended such that its curvature substantially matches that of the back of a patient 50. The principle can be extended to any anatomical part of a body in order to fit its external shape. In this case, the abovementioned attachment fixture may be omitted. Radiopaque markers 80 are attached to support structure 78. The advantage of this phantom design is the fact that the Region Of Interest (ROI) is surrounded by radiopaque markers while keeping the ROI itself free, thus allowing unobstructed surgical access to the ROI by the surgeon while maximizing the number of markers being close to the ROI and imaged during the scan.

While in theory a phantom with only one marker detectable in at least two images can already increase the quality of the resulting 3D reconstruction, using more phantom markers increases the accuracy of calibration and therewith the quality of the reconstructed 3D volume.

On the other hand the likelihood of mutual marker superimpositions in the 2D X-ray images is increased at the same time.

Since fully or partially superimposed marker shadows make it more difficult or even impossible to identify them and detect their position accurately, their useful number is limited.

In a preferred embodiment, at least half of the acquired images contain at least five detectable markers and a small percentage of images are non-reference images. For a typical phantom design as shown in FIG. 3, a reasonable number of markers 64 is between five and fifteen. They are placed on support structure 66 such that the coordinate along axis 65 is different for each marker. For a typical orbital scan movement the phantom is positioned such that axis 65 is essentially parallel to the orbital rotation axis of imaging system 20. Even if both axes are not perfectly parallel, superimposition of marker shadows can be avoided.

During a 3D scan, a set of 2D X-ray images is taken at different predetermined positions of imaging system 20 with respect to patient 50.

In one preferred embodiment, the movement of imaging system 20 during the scan is a motor-driven pure orbital rotation with all other degrees of freedom being locked, including the floor movement with rollers 30, while the predetermined positions correspond to equidistant orbital joint positions being measured with position encoders.

It is important to note, however, that the scope of the invention is not limited to this scan movement and works in the same manner for multi-dimensional scan movements and non-equidistant scan positions.

For each predetermined position corresponding to a set of position encoder values for all joints of imaging system 20, the position of the focal point of X-ray source 22 and the position and orientation of image detector 24 are determined in a coordinate system 29 linked to chassis 28 (see FIG. 1b) prior to the clinical use and are stored in a look-up table (LUT).

These data yielding the nominal projective geometry data, i.e. the data that describe the default projection geometry of the imaging system known by design, metrology or offline calibration without taking into account alterations of these default projection geometry data from the real geometry during the image acquisition and caused by material fatigue, mechanical deformations, vibrations, mechanical play, etc., can be gathered in different ways.

In one preferred embodiment, these nominal projective geometry data are determined prior to the clinical use of the C-arm with an offline calibration phantom as known in the state of the art.

Using such a calibration method has the advantage of taking into account reproducible position deviations of X-ray source 22 and image detector 24 over values only known by design.

As it will be described, the invention is advantageously carried out using markers.

To that end, a calibration phantom containing radiopaque markers is used. In such an embodiment, generating a 3D image comprises the following steps:

a) In a preliminary step which is not intended to be covered as such by the present invention, calibration phantom 48 is attached to the patient such that the radiopaque markers are close to the ROI i.e. the anatomical region the 3D image whereof shall be reconstructed.

At least two 2D X-ray images must contain at least one detectable radiopaque marker, although typically more than two images contain more than one marker.

However, in the case of only two images, each containing only one detectable marker, said images must be sufficiently angled with respect to each other to provide sufficient projective out-of-plane information with the second image with respect to the first image to improve the 3D reconstruction by the calibration. In practice the angle between the two images should be at least 15°.

Imaging system 20 is then positioned and its joints are adjusted such that the orbital rotational movement around the ROI required for the scan can be carried out without any collision between the imaging system and the patient, the phantom, the patient table or any other physical object present in the vicinity. Note that the orbital rotational movement can be replaced by a complex trajectory of the C-arm.

b) Then a set of X-ray projection (2D) images is acquired at said predetermined positions during an orbital rotation of imaging system 20. Said set of images may be stored in a memory of the data processing unit.

c) In a next step all 2D images are searched for marker shadows that allow automatic identification of the corresponding phantom markers by the data processing unit, using standard image processing techniques that calculate the coordinates of the center of an object in a grey level image using all the pixels (weighted by their grey level value or simply the pixels above a threshold assigned to a fixed value) belonging to the object. For ball shaped markers for example, the data processing unit checks the images for closed contours and assesses the circularity and size of the identified closed contours. Further details can be found in U.S. Pat. No. 6,370,224 or U.S. Pat. No. 5,442,674 for example. Similar techniques are used to detect the centers of lines or curves (i.e. the middle of said lines or curves) that correspond to projections of markers made of cylinders or tubes. Well-known techniques are used to detect the edges of coils of electromagnetic sensors or transmitters that constitute markers.

Calculation of the precise position of the identified marker shadow in the 2D image is carried out by the data processing unit by computing its center as described in (14, 15) for example.

Those images in which at least one of the markers can be detected automatically, i.e. in which for at least one of the phantom markers a set of pixels in the image can be assigned to it and its position can be determined, are called reference images.

The remaining images, i.e. the images in which no marker can be detected automatically, are called non-reference images.

Indeed, for several reasons, not all of the markers will be identifiable in practice in all the images of the acquired set, and thus not all projection images will be reference images. Taking into account this phenomenon is a basis for the present invention.

First, one or more markers may be fully or partially outside the field of view of the detector for one, more or all projection images.

Second, one or more of the markers may superimpose mutually in one or several of the projection images.

Third, one or more markers may overlap with other radio-dense objects within one or more of the projection images such as metal surgical instruments, the operating table, patient dense structures such as bones, etc. The use of contrast agents reinforces this difficulty.

Fourth, one or more markers may be in an image area which is blurred or over-exposed by x-rays or with a low signal-to-noise ratio, which make them undetectable.

For each reference image, the 2D position of each identified marker within that image is calculated using the abovementioned image processing techniques.

In a next step an optimal rigid transformation between the coordinate systems 29 and 49 is computed.

In one embodiment, this optimal transformation is computed using a feature-based 2D/3D registration technique which minimizes the sum of the squares of the distances for all detected markers between the back-projection rays calculated from the 2D positions of said detected markers in each reference image using the respective nominal projective geometry data of this image and the known 3D position of the corresponding phantom marker in the coordinate system of the calibration phantom, by adjusting the standard six transformation parameters between 29 and 49. Such minimization of the sum of the squares of the distances between 3D lines and 3D points known in two distinct coordinate systems can be achieved using the Iterative Closest Point algorithm published in (16) or any of its variations using for example the Levenberg-Marquardt algorithm. The reliability of this method can be improved using any well-known robust algorithm that eliminates outliers.

In another embodiment, this optimal transformation is computed by minimizing the distances for all detected markers between the 2D positions of said detected markers in each reference image and the position of the projection of the 3D position of the respective marker onto said reference image calculated from the respective nominal projective geometry data of this image by adjusting the six transformation parameters between 29 and 49. The reliability of this method can be improved using any well-known robust algorithm that eliminates outliers.

In one embodiment, the calibration phantom contains only a single marker. In this case the transformation between 29 and 49 involves translation only and the rotation values are then assigned a zero default value.

In one embodiment, the calibration phantom contains only two markers. In this case the transformation between 29 and 49 involves translation and rotation around two degrees-of-freedom, a rotation around one axis being undetermined and assigned a zero default value.

Reference images can be defined as those images containing at least a given number NB of phantom markers that can be detected automatically, with NB>0. The higher NB is, the more accurate will be the adjustment applied to the nominal projective geometry data described further, but the lower is the number of reference images. Selecting a number NB depends on the particular context of use of the invention. In some cases, the number of radiopaque markers usually detected in each image can be very high and therefore it is recommended to select a value of NB which is close to the total number of markers that constitute the calibration phantom. For example, if the calibration phantom is made of eight radiopaque balls, assign NB to a value of seven. In more complex cases, the number of radiopaque markers usually detected in each image can be very low, and therefore it is recommended to select a value of NB which is one or two.

In a preferred embodiment, the number NB of markers that defines a reference image versus a non-reference image can be assigned a low value such as one for the first iteration of the global method of the invention and then the global method can be repeated, whilst the number NB is increased to a superior value. This process can be repeated and iterated several times.

d) In a next step the nominal projective geometry data for each reference image are adjusted such that its associated 2D marker shadow positions match optimally the 2D positions of the transformed 3D phantom marker positions when projected onto the image.

In one embodiment the adjustments applied to the nominal projective geometry data for each reference image are limited to the two coordinates of the X-ray source in a plane parallel to the image detector. This involves searching for two independent parameters for each 2D image. In another embodiment, the adjustments of the nominal projective geometry data include the three coordinates of the X-ray source and the complete position and orientation of the image detector represented by a matrix or six independent rotation/translation parameters, as well as the scaling factors in the image to determine the pixel to millimeters ratio (one or two ratios, depending on a priori information about the image detector). This involves searching for ten or eleven independent parameters for each 2D image.

In another embodiment, an intermediate number of parameters is adjusted for each image, ranging from two to eleven.

This way the projective geometry is inventively corrected in order to compensate for non-reproducible positioning deviations of source 22 and detector 24 not covered by the nominal projective geometry data.

In the invention, we recommend the use of a fully digital flat panel image detector, which has the advantage over conventional image intensifiers of avoiding any geometric image distortion. However, if conventional image intensifiers are used, it might be also necessary to consider in the nominal projective geometry data a distortion compensation model, which is usually a polynomial function between pixel image coordinates and coordinates in an image plane expressed in millimeters. In the latter case, the adjustment of the nominal projective geometry data geometry may have to include an adjustment of the coefficients of the corresponding polynomial function, but this will require using many markers. It is therefore preferable in practice to ignore the adjustment of the polynomial function and adjust only the parameters that correspond to rigid deformations as described previously. However, in that case, it is preferable to calculate and store in the nominal parameters a polynomial function with coefficients that vary with the orientation of the C-arm because it is known that the distortion varies considerably with the C-arm orientation (this is due to the impact of magnetic fields and mechanical deformation of the C-arm). This is simply achieved during offline calibration by using a rigid planar grid fixed to the C-arm detector and calibrating the polynomial functions for various orientations of the C-arm, optimally taking into account a magnetometer to detect the orientation of magnetic fields. Optimizing the 11 or 12 parameters of the model for each online image using the method of the invention will then compensate partially for some amount of the variation of the distortion with respect to the nominal parameters. Another solution is to fix a planar grid with multiple markers on the C-arm permanently and detect those markers separately from the phantom markers in order to calculate a polynomial function for each image on-line.

e) A first 3D image can now be computed within the coordinate system 29, using standard tomographic reconstruction techniques known in the art, such as Filtered Back Projection or Algebraic Reconstruction Techniques.

A reconstructability criterion is used to decide which projection images of the acquired set of images are used for this first reconstruction of the 3D image.

The reconstructability criterion is determined empirically and depends on the number and the angular distribution of the reference images.

The reconstructability criterion can be defined as a test comprising the following items:
Are there sufficient reference images?
Is the angular coverage of the reference images sufficient?
Is the angular distribution of the reference images sufficiently uniform?

If the criterion is met (i.e. the response to each of the above items is yes), only the reference images with their corresponding adjusted projective geometry data are used for the initial reconstruction of the 3D image.

If, on the other hand, the criterion is not met (i.e. the response to at least one of the above items is no), a reconstruction based only on the reference images would not provide a good result. For example, if reference images are all obtained inside an angular range of ninety degrees or less, it is known that the reconstruction process will provide a poor quality 3D image. In a preferred embodiment, in order to provide a sufficient quality of the initial 3D image, the reconstruction is carried out using not only the reference images with their corresponding adjusted projective geometry data but also the non-reference images with their corresponding nominal projective geometry data.

In another preferred embodiment, projective geometry data of the non-reference images are adjusted and computed by interpolation of the projective geometry data of the reference images surrounding said non-reference images. A 3D reconstruction is then performed using all adjusted projective geometry data.

In another preferred embodiment, the reconstruction is carried out using all images using their nominal projective geometry data.

It is possible to stop the method at the end of that step, depending on the desired accuracy, the reconstructability criterion, and the selected embodiment. However, the method proposes to perform additional steps to increase the accuracy and quality of the reconstructed 3D image.

f) In a next step, whether the 3D image has been reconstructed only with the reference images or not, said 3D image is projected onto each non-reference image using their respective nominal projective geometry data.

Subsequently 2D-2D image grey level/intensity-based registration techniques using well-known image similarity measures such as mutual information, joint entropy or cross correlation ratio are applied to each non-reference image and its respective projected 3D image in order to adjust said nominal projective geometry data of said non-reference images. For example, one of the numerous 2D-2D image registration methods described in M. P. Deshmukh & U. Bhosle, a survey of image registration. International Journal of Image Processing (IJIP), Volume (5): Issue (3), 2011 or in Oliveira F P, Tavares J M, Medical image registration: a review. Comput Methods Biomech Biomed Engin. 2012 Mar. 22, can be applied.

In one embodiment, the adjustments to the projective geometry data associated to each non-reference image are limited to in-plane translations and rotation of the image detector, which corresponds to finding three independent parameters for each 2D-2D image registration.

In another embodiment, only the translation parameters are adjusted, which reduces the risk of erroneous adjustments.

In another embodiment, a 2D-2D transform involving more than three independent parameters is defined, for example an affine transform, or a warping transform that displaces the four corners of the image independently.

g) An updated more accurate 3D image is then computed using the complete set of 2D images with corresponding adjusted projective geometry data.

In one embodiment, one or several steps of the method described above are iterated until a registration quality measure is below a predetermined threshold (for example, a quality measure can be the contrast or sharpness of the 3D image) or a predetermined number of iterations has been reached (for example, one iteration, or three iterations).

In one embodiment, the reconstructed 3D position of markers and/or the adjusted projective geometry data can be used to iterate on the search and detection of radiopaque markers using an estimation of the theoretical position of said markers in the image to initiate the next search. It has the advantage of increasing the number of detected markers for the next iteration of the global method and therefore it is likely to improve the accuracy of the reconstructed image. By this mechanism, the minimum number NB of markers that define reference images versus non-reference images can be progressively increased at each iteration.

In another embodiment, only steps (f) and (g) are iterated to improve the quality of the final reconstructed 3D image.

The reconstructed 3D image can then be transmitted to a graphic display in order to be visualized.

The reconstructed 3D image can also be stored in a memory of the data processing unit for further use.

If the calibration phantom contains a localization device that is detected by a navigation system (for example an electro-magnetic sensor or transmitter, or an optical tracker), the resulting 3D image is directly transferred and used for navigation of instruments inside the 3D image.

In any of the embodiments, the calculated adjusted projective geometry data that are obtained at the end of a 3D reconstruction can be stored in order to update the previous nominal projective geometry data for further use. Further use can occur the same day for the same patient or several days after for another patient. It is then possible to track the evolution of the projective geometry data, which offers useful indicators for the maintenance of the device. For example, sudden and considerable variations of the projective geometry data probably correspond to a shock or a mechanical modification that requires further inspection of the device.

Figure 7:
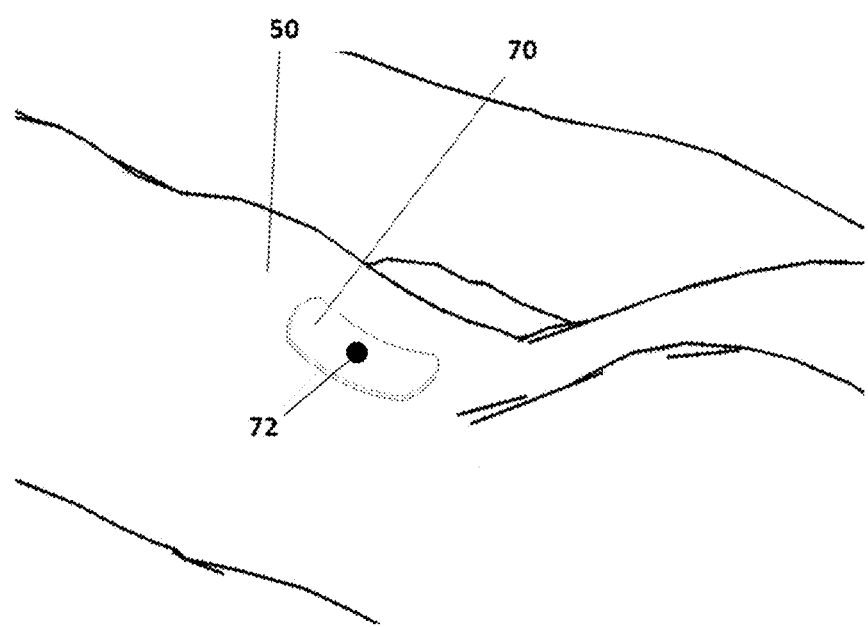
FIG. 7 schematically illustrates an exemplary embodiment of a phantom with one ball-shaped radiopaque marker.

In order to illustrate the method with a preferred embodiment, the method is described for a phantom made of only one marker. In this example, the marker is a stainless steel spherical ball four millimeters in diameter (see FIG. 7). The marker 72 is simply fixed to the skin of the patient 50 in a region to be imaged, by using an adhesive tape 70 as for electrocardiogram skin electrodes. In this example, it is assumed that the skin does not move significantly relatively to the anatomical structure of interest. A series of one hundred and ninety images is acquired, at every degree of an orbital rotation of the C-arm. A flat panel image detector is used. Each image is analyzed by the computer and the metal ball is searched for. But because of various phenomena, such as overexposure in some areas, it is likely that the ball cannot be automatically and accurately detected on all images. In this example it is assumed that the ball is not detected in images pertaining to an angular sector of thirty degrees (non-reference images), and automatically detected in all other images (reference images). It is assumed that the reconstructability criterion is met. Using the nominal projective geometry of the reference images, the center of the projection of the spherical ball is back projected in 3D. The intersection of the back-projection lines defines a 3D point that is defined as the center of the 3D spherical ball. An optimal rigid transformation between the coordinate system of the X-ray imaging system and the coordinate system of the calibration phantom is simply defined by a translation that aligns the calculated center of the 3D spherical ball with the origin of the X-ray imaging system coordinate, and a rotation component equal to the identity matrix. Said 3D spherical ball is then projected on each image and a translation is applied to each image to match the projection of said 3D spherical ball with the true position of the ball center on the image. The nominal projective geometry data of the reference images are therefore adjusted by a translation in the image plane. A first 3D image reconstruction is then performed using only the reference images with their adjusted projective geometry data. The resulting 3D image is then projected on all non-reference images and a 2D-2D image registration is performed between the real images and the projected images of the 3D image, for those non-reference images only. It generates a translation and a rotation of each image, which corresponds to three adjusted parameters of the projective geometry data. To accelerate the process, the registration is performed by only considering a central area of each real image. If the registration provides an uncertain result given by a low registration score given by conventional criteria of image-to-image registration techniques, the registration is ignored and the nominal projective geometry data are taken into account. The result of this step is a new set of adjusted projective geometry data for all images. A second 3D reconstruction is then performed using said adjusted projective geometry data applied to all images. This second projective geometry data have a better accuracy and quality than the reconstruction that would have been performed using the nominal projection geometry data.

Figure 6:
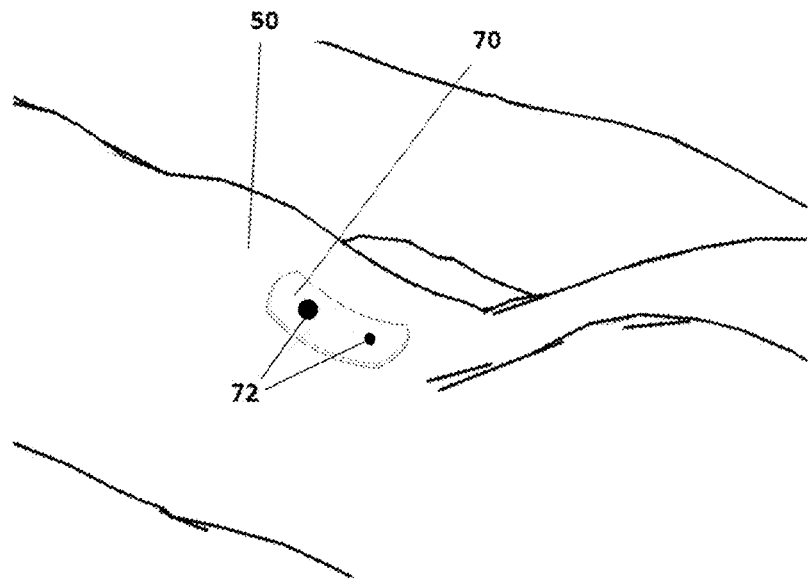
FIG. 6 schematically illustrates an exemplary embodiment of a phantom with two ball-shaped radiopaque markers having different diameters.

In another example, the calibration phantom is made of two spherical markers (see FIG. 6). The two balls 72 are placed in a direction parallel to the body of the patient 50 and attached by using an adhesive tape 70, and an image acquisition is performed around the body. It has the advantage that the projection of both balls will not overlap each other, and it generates more accuracy than using only one ball. The same method as described previously is applied, the only difference is (a) that the search for two balls with a fixed relative geometry is more reliable than only one ball and (b) that the adjusted projection geometry parameters obtained in the first step correspond to a rotation and a translation of the image, and not only a translation. It is also possible to maintain only a translation and obtain a more accurate registration of the balls by using a least squares technique. Advantageously, as illustrated in FIG. 6, the two balls have different diameters.

In a third example, the calibration phantom is made of four balls and six pins. The six pins are used to rigidly attach the calibration phantom to a vertebra using transcutaneous pin fixations, three pins on each side of the vertebra. The four balls are covered by a reflective material and they constitute a rigid body detected by an optical localizer. This rigid body constitutes the patient reference system. The coordinates of the balls and pins are all known in a unique calibration phantom coordinate system which is identical to the patient reference system. A series of one hundred and ninety images are acquired, at every degree of an orbital rotation of the C-arm. Each image is analyzed by the computer and the metal balls and pins are searched for. In some images, at least three balls are detected and labeled automatically; they constitute the reference images. The other images constitute the non-reference images. For all reference images, the detected balls and pin segments are back-projected using nominal projective geometry data. For each image, said back-projections are registered with the 3D coordinates of the balls and pins expressed in the calibration phantom coordinate system. It generates a transform matrix between the calibration phantom coordinate system and the coordinate system of the C-arm in which the nominal projective geometry data have been defined. For each image, the 3D balls and pins are projected on the image and projective geometry data are adjusted to match them using a least-squares criterion that minimizes the sum of the squares of the distances between the theoretical projections of the balls and the pins and their real extraction on the image. In this example, both the X-ray source and the image origin are translated equally, and in addition a rotation of the image plane is adjusted. Then, the rest of the procedure is equivalent to the previous examples. However, it is then possible to navigate a surgical instrument equipped with reflective spheres and visualize its position in real time on the resulting 3D image since the image is reconstructed directly in the coordinate system of the calibration phantom which is itself directly the coordinate system of the patient reference system.

In a fourth example, the acquisition of images is taken just after implants such as pedicle screws have been inserted in a patient body, in order to check their location. There are no additional markers attached to the patient. The calibration phantom is directly made of the implants which constitute markers having a partially known geometry. Metal implants are particularly well visible on images. For example, four pedicle screws are observed on images after two vertebrae have been operated. The individual geometry of the implant is known and stored in the computer. But the relative geometry between the implants is left unknown. In a first step, all images where the implants can be detected and identified separately are selected, and the three-dimensional position and orientation of each implant is reconstructed using the projections detected on those images using a 3D/2D rigid registration algorithm. The calibration phantom is now perfectly and entirely known. Then the rest of the method follows. The advantage of this method in this example is to obtain a clear and precise 3D image of the bones with the implants, with a high degree of precision and sharpness, which facilitates the decision to let the implants at their current position or to re-operate on some of them.

According to another embodiment of the invention, a series of one hundred and ninety images is acquired, at every degree of an orbital rotation of the C-arm, but no markers are detected on the 2D images. This may be because the patient has characteristics such as a large volume that create poor quality images. This may also be the case if the calibration phantom was forgotten by the user. This may also be the case simply because the user does not want to take the time and effort to position a calibration phantom, even if it is non-invasive and compact. In that example, the first part of the method described above cannot be applied since there are no markers at all, or no detectable markers. It is then possible to apply only the second part of the method (wherein all images are non-reference images). First, a 3D image is reconstructed using the nominal projective geometry data associated with all 2D images that have been acquired. Second, the reconstructed 3D image is projected onto each 2D image still using the nominal projective geometry data; it constitutes a virtual grey-level image. This projection step can benefit from graphical processing units (GPU) for example using programming in the Cuda language to accelerate the process. For each 2D image, a 2D-2D image registration method is applied between the real 2D image and the projection of the 3D image. For example, the optimal rigid transform consisting of one 2D translation and one rotation (three parameters) is searched such that the mutual information of both images is maximized in a predefined region of interest, using techniques that are for example described in Oliveira F P, Tavares J M, Medical image registration: a review, Comput Methods Biomech Biomed Engin. 2012 Mar. 22. To define the region of interest, a possible solution is to search in the first reconstructed 3D image for the voxels that have a high contrast after filtering noise, to identify the centroid of such high-contrast voxels, and to project said centroid on the 2D image, with a bounding box around the resulting projected point that has an a priori size such as half of the total image size in each dimension (the 3D image volume is then divided by eight). To accelerate the process of registration, conventional multi-level registration techniques can be used, for example using wavelets or just pyramids. For each image, the three adjusted parameters are obtained, and a second 3D reconstruction is performed using all images with their adjusted projective geometry data. Depending on the accuracy required by the application, the method can be iterated if necessary. In that case, the second 3D reconstructed image is projected on all 2D images and a 2D-2D registration is performed again between the real images and the projections of the second 3D reconstructed image. This yields a new set of adjusted projective geometry data. A third reconstruction is performed using the corresponding adjusted projective geometry data. The method can be iterated as many times as necessary, depending on the accuracy required and time limitations. A fixed number of iterations can be preset, or a contrast criterion can be calculated on the reconstructed 3D image and the process is stopped when said criterion is above a given threshold, which will have the advantage of producing a 3D image always having good sharpness.

As stated above, the method can be carried out with or without the use of markers. Using markers reinforces the stability and accuracy of the method and it is required anyway if the 3D image is used for navigation. Not using markers is of course simpler for the user but it requires that the initial nominal projective geometry data be reasonably close to the true projective geometry data such that the convergence of the method will be ensured. Using markers does not have this drawback. Eventually, the method can be used in a large variety of applications, for a large variety of x-ray system architectures, during diagnostic imaging or during surgery, with or without link to navigation, for any part of the body. It can be used also for non-medical applications such as non-destructive checking of objects using devices containing x-ray flat panel detectors instead of standard Computed Tomography. The method proposed in this invention offers multiple parameters and options that are adjusted according to each situation.

REFERENCES

1. Feldkamp, L. C. Davis, L W. Kress. Practical cone-beam algorithm. J. Optical Society of America. A 1984, 1, pp: 612-619; Yves Trouset, Didir Saint-Felix, Anne
2. Rougee and Christine Chardenon. Multiscale Cone-Beam X-Ray Reconstruction. SPIE Vol 1231 Medical Imaging IV: Image Formation (1990); B. D. Smith, "Image reconstruction from cone-beam projections: necessary and sufficient conditions and reconstruction methods".
3. Grass, M. et al. Three-dimensional reconstruction of high contrast objects using C-arm image intensifier projection data. Computerized medical imaging and graphics the official journal of the Computerized Medical Imaging Society 23, 311-321 (1999).
4. Stübig, Timo et al. "Comparative study of different intra operative 3-D image intensifiers in orthopedic trauma care." The Journal of Trauma 66.3 (2009): 821-830.
5. Kendoff, Daniel et al. "Limitations and pitfalls of 3-D fluoroscopic navigation in orthopaedic trauma surgery." Technology and health care official journal of the European Society for Engineering and Medicine 17.2 (2009): 133-140. Print.
6. Wendl, K et al. "Iso-C (3D0-assisted) navigated implantation of pedicle screws in thoracic lumbar vertebrae." Der Unfallchirurg 2003: 907-913. Print.

7. Siewerdsen, J H. "Cone-beam CT with a flat-panel detector on a mobile C-arm: preclinical investigation in image-guided surgery of the head and neck." Proceedings of SPIE 5744.II (2005): 789-797.
8. Siewerdsen, J H et al. "Volume CT with a flat-panel detector on a mobile, isocentric C-arm: pre-clinical investigation in guidance of minimally invasive surgery." Medical Physics 32.1 (2005): 241-254.
9. Nakashima, Hiroaki et al. "Comparison of the percutaneous screw placement precision of isocentric C-arm 3-dimensional fluoroscopy-navigated pedicle screw implantation and conventional fluoroscopy method with minimally invasive surgery." Journal of spinal disorders techniques 22.7 (2009): 468-472.
10. Powell, Michael F, Diane DiNobile, and Arra S Reddy. "C-arm fluoroscopic cone beam CT for guidance of minimally invasive spine interventions." Pain Physician 2010 51-59.
11. Kotsianos, Dorothea et al. "3D imaging with an isocentric mobile C-arm comparison of image quality with spiral CT." European Radiology 14.9 (2004): 1590-1595.
12. Hüfner, Tobias et al. "Utility of intraoperative three-dimensional imaging at the hip and knee joints with and without navigation." The Journal of Bone and Joint Surgery 91 Suppl 1 (2009): 33-42.
13. LixuGu, Terry Peters. "3D Automatic Fiducial Marker Localization Approach for Frameless Stereotactic Neurosurgery Navigation." Proceedings of the International Workshop on Medical Imaging and Augmented Reality MIAR (2004), Pages 329-336
14. Bose, C. B. and Amir I. (1990): Design of fiducials for accurate registration using machine vision, IEEE Transactions on Pattern Analysis and Machine Intelligence, Vol. 12, n. 12, pp. 1196-1200.
15. P. Besl and N. McKay. A method for Registration of 3-D Shapes. *IEEE Transactions on Pattern Analysis and Machine Intelligence (PAMI)*, 14(2): 239-256, February 1992
16. M. P. Deshmukh & U. Bhosle, A survey of image registration. International Journal of Image Processing (IJIP), Volume (5), Issue (3), 2011
17. Oliveira F P, Tavares J M. Medical image registration: a review. Comput Methods Biomech Biomed Engin. 2012 Mar. 22.
U.S. Pat. No. 6,715,918B2: Calibration phantom for projection X-ray systems
U.S. Pat. No. 5,442,674: Device and automatic method for the geometrical calibration of an X-ray imaging system
U.S. Pat. No. 6,038,282: X-ray imaging system
U.S. Pat. No. 6,079,876: X-ray exposure system for 3D imaging
U.S. Pat. No. 6,120,180: X-ray exposure system for 3D imaging
DE 10139343: Verfahren and Vorrichtung zur Bestimmung der Position des Fokuspunktes einer Röntgenstrahlenquelle
U.S. Pat. No. 7,494,278: Method for correcting non-reproducible geometric errors occurring during the operation of an x-ray C-arm device
U.S. Pat. No. 6,370,224: System and methods for the reduction and elimination of image artifacts in the calibration of x-ray imagers
U.S. Pat. No. 5,442,674: Device and automatic method for the geometrical calibration of an X-ray imaging system
U.S. Pat. No. 7,672,709: Determination of the position of a radiographic or radioscopic unit

The invention claimed is:

1. A method for reconstructing a 3D image from 2D X-ray images acquired with an X-ray imaging system, said method comprising the steps of:
   a) receiving a set of 2D X-ray images of a region of a patient with said X-ray imaging system,
   b) computing an initial 3D image within the coordinate system of the X-ray imaging system by using the complete set of 2D X-ray images with their respective projective geometry data;
   c) projecting said initial 3D image on each of said 2D X-ray images and adjusting the respective projective geometry data of said 2D X-ray images by registration of each 2D X-ray image with the projection of the initial 3D image using an image-to-image registration technique which determines an affine transform or a warping transform that displaces the four corners of each image independently;
   d) computing an updated 3D image using the complete set of 2D X-ray images with their respective adjusted projective geometry data.

2. The method of claim 1, wherein one or several steps (b) to (d) are iterated.

3. The method of claim 1, wherein the calculated adjusted projective geometry data of each image are used as the updated nominal projective geometry data for further 3D image reconstruction.

4. The method of claim 1, wherein the evolution of the projective geometry data is tracked.

5. The method of claim 1, wherein in step (c) the registration of each 2D X-ray image with the projection of the initial 3D image is made in a predefined region of interest.

6. The method of claim 1, wherein a contrast criterion is calculated on the reconstructed 3D image and the method is stopped when said criterion is above a given threshold.

* * * * *